US005739361A

United States Patent [19]

Signor et al.

[11] Patent Number: 5,739,361
[45] Date of Patent: Apr. 14, 1998

[54] PROCESS FOR THE PREPARATION OF FUROSEMIDE

[75] Inventors: Angelo Signor, Padua; Alfredo Guerrato, Trissino; Giovanni Signor, Padua, all of Italy

[73] Assignee: Proteos S.r.L., Padua, Italy

[21] Appl. No.: 817,569

[22] PCT Filed: Oct. 23, 1995

[86] PCT No.: PCT/EP95/04153

§ 371 Date: Apr. 23, 1997

§ 102(e) Date: Apr. 23, 1997

[87] PCT Pub. No.: WO96/12714

PCT Pub. Date: May 2, 1996

[30] Foreign Application Priority Data

Oct. 24, 1994 [IT] Italy .................... MI94A2171

[51] Int. Cl.⁶ .................... C07D 307/54; C07C 25/13
[52] U.S. Cl. ............................. 549/494; 570/127
[58] Field of Search ................ 549/494; 570/127

[56] References Cited

U.S. PATENT DOCUMENTS 3,058,882  10/1962  Stürm et al. ...................... 549/494

FOREIGN PATENT DOCUMENTS

| 0 093 976 | 11/1983 | European Pat. Off. |
| 1 396 621 | 4/1963 | France . |
| 1 220 436 | 1/1968 | Germany . |
| 1 806 581 | 6/1971 | Germany . |

OTHER PUBLICATIONS

*Chemische Berichte*, vol. 99, No. 1, 1966, Weinheim, Germany, pp. 328–344, K. Sturm, et al, "Synthesen von 5–Sulfanyl–anthranilsäure–Derivaten".

*Chemical Abstracts*, vol. 64, 1966, "Heterocyclic Compounds," pp. 8113–8116.

Primary Examiner—Bernard Dentz
Attorney, Agent, or Firm—Lowe, Price, LeBlanc & Becker

[57] ABSTRACT

A new process for the preparation of furosemide [4-chloro-N-(2-furylmethyl)-5-sulfamoyl-anthranilic acid] comprising the photochlorination of 4-chloro-2-fluoro-toluene to give 4-chloro-2-fluoro-benzotrichloride, the aminosulfonylation of the same and the subsequent condensation with furfurylamine.

10 Claims, No Drawings

PROCESS FOR THE PREPARATION OF FUROSEMIDE

This application is a 371 of PCT/EP95/04153 filed Oct. 23, 1995 published as WO96/12714 May 2, 1996.

FIELD OF THE INVENTION

The present invention relates to a new and effective process for the preparation of 4-chloro-N-(2-furylmethyl)-5-sulfamoyl anthranilic acid, or furosemide, an active ingredient which has been known since long as a diuretic and antihypertensive in human therapy and as a diuretic for the treatment of animals.

PRIOR ART DISCLOSURE

Furosemide, one of the main members of the class of diuretic sulfonamides, acts simultaneously as an inhibitor of urine dilution and concentration. One of the advantages offered by said diuretic consists in its short times of action, which allow an easy control of diuresis by properly adjusting doses and administration frequency.

According to U.S. Pat. No. 3,058,882, furosemide is prepared from 2,4-dichlorobenzoic acid, which is chlorosulfonated with sulfuric chlorohydrin and then ammonolyzed. Treatment of the resulting sulfonamide with furfurylamine yields furosemide in low yields (35 to 50%). Other methods envisaging the condensation of furfurylamine with some 5-sulfamoyl-benzoic acid derivatives, such as esters, amides (DE 1 220 436; Derwent abstract) and nitriles (DE 1 806 581; Derwent abstract), are also described. However, these methods require a final hydrolysis of the carboxylic acid derivative.

All the above synthetic routes include a scarcely effective condensation step with furfurylamine yielding several by-products; as a consequence the yield is low and the purification of the final product is difficult. As disclosed in FR patent 1,396,621, practically quantitative yields may be obtained through the condensation of 4-chloro-2-fluoro-5-sulfamoyl-benzoic acid with furfurylamine. Nevertheless, the above mentioned fluoro-derivative is synthetized by chlorosulfonylation of 4-chloro-2-fluoro-benzoic acid and subsequent ammonolysis of the obtained product, showing only poor total yields (Chem Abstr. Vol. 64, 8112–8116, 1966) and rendering the process economically unprofitable.

The European patent application EPA 0 093 976 describes the photochlorination of 2-chloro-4-fluoro-toluene to give 2-chloro-4-fluoro-1-benzotrichloride.

SUMMARY OF THE INVENTION

The claimed invention relates to a process for the preparation of furosemide having the following structural formula (I):

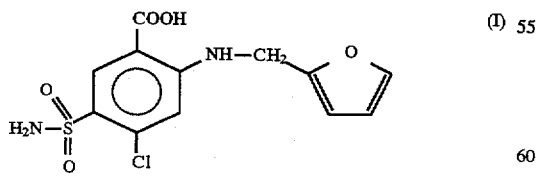

Said process comprises the following reaction steps:

A) 4-chloro-2-fluoro-toluene (II) is photochlorinated to give 4-chloro-2-fluoro-benzotrichloride (III), unknown in the state of the art and essential for the following steps;

B) 4-chloro-2-fluoro-benzotrichloride (III) obtained in step A) is chlorosulfonylated by treatment with sulfuric chlorohydrin in the presence of sulfuric acid and the resulting product is ammonolyzed by tratment with ammonium hydroxyde to give 4-chloro-2-fluoro-5-sulfamoylbenzoic acid (IV):

C) finally, 4-chloro-2-fluoro-5-sulfamoylbenzoic acid (IV) obtained in step B) is condensed with furfurylamine to give furosemide (I).

The reaction scheme is as follows:

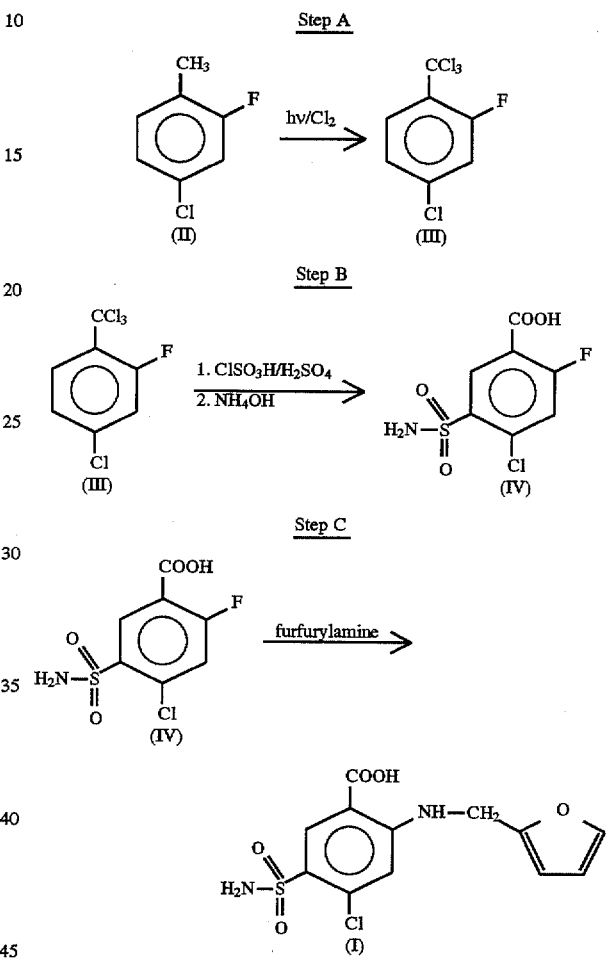

DETAILED DESCRIPTION OF THE INVENTION

The characteristics and advantages of the process for the preparation of furosemide (I) according to the present invention will be better illustrated in the following detailed description.

Step A:

in an apparatus properly equipped for photochemical chlorination, 4-chloro-2-fluoro-toluene (II) is treated with gaseous chlorine which is bubbled at a flow rate of 12 g/h to 16 g/h per mole of (II), preferably 14 g/h, at a temperature of 85° C. to 95° C., preferably 90° C., for a period of 11 to 12 hrs. to give 4-chloro-2-fluoro-benzotrichloride (III), a product unknown in the state of the art.

Such a new product, easily obtainable industrially with high purity and high yields by means of the above photochlorination, plays a key role in the economy of the total process. It is to be stressed the fact that this intermediate consents to obtain very high process yields in the following reaction steps; this is mainly due to the presence of the group —CCl$_3$, particularly advantageous in the chlorosulfonylation reaction.

Step B:

4-chloro-2-fluoro-benzotrichloride (III), obtained in step (A), is caused to react with sulfuric chlorohydrin at a sulfuric chlorohydrin/(III) molar ratio not lower than 4, preferably ranging from 4 to 10, in the presence of sulfuric acid, at a (III)/sulfuric acid molar ratio ranging from 1.0 to 1.3. The compound (III) is slowly added to a mixture of sulfuric chlorohydrin and sulfuric acid, in the above molar ratios, suitably preheated at a temperature ranging from 60° to 140° C., taking care to entrap gaseous HCl. The reaction mixture thus obtained is maintained at a temperature ranging from 140° C. to 150° C., for a period ranging from 1 to 3 hrs.

The reaction mixture is quenched in water at a temperature of 0°–2° C. under stirring and then maintained at room temperature for a period ranging from 4 to 10 hrs, preferably of 6 hrs; at the end of said period, the hydrolysis of the —CCl$_3$ group to —COOH is already completed. The resulting product is 4-chloro-2-fluoro-5-chlorosulfonylbenzoic acid. After filtration and water washings, the crude chlorosulfonylbenzoic acid can be kept in dry form in the cold for several weeks without undergoing considerable decomposition.

The product is directly added, under stirring, to a solution containing ammonium hydroxide in excess compared with (III), preferably at a NH$_4$OH/(III) molar ratio ranging from 13 to 25, maintaining the temperature in the range of 0° C. to 10° C., and allowed to react for a period of 1–5 to 2 hrs. After filtration and evaporation at a temperature lower than 10° C., taking care to avoid heating in order to hinder any possible nucleophilic replacement of fluorine, the complete precipitation of the product is obtained by cooling, according to common procedure.

4-Chloro-2-fluoro-5-sulfamoylbenzoic acid (IV), a white to slightly yellow product, with purity of 94–97% as determined by HPLC, is isolated. According to another embodiment of step (B) of the present invention, dichloromethane is added to the water reaction mixture containing 4-chloro-2-fluoro-5-chlorosulfonyl-benzoic acid, obtained from the reaction of chlorosulfonylation, approximately half in volume of said water mixture.

According to another possibility, the same wet 4-chloro-2-fluoro-5-chlorosulfonyl-benzoic acid, obtained from the filtration of said water mixture, can be dissolved in dichloromethane.

The organic phase consisting of 4-chloro-2-fluoro-5-chlorosulfonylbenzoic acid in dichloromethane is separated from the aqueous phase and washed with cold water; the combined aqueous phases are discarded. The organic phase is added directly to a concentrated ammonia solution, as described above, with an easy control of the temperature and the possibility of solvent recovery. The excess of ammonia can be partially eliminated by stirring under vacuum and maintaining the temperature below 10° C. The obtained solution can be subsequently acidified (pH 2.0) with 30% H$_2$SO$_4$.

4-Chloro-2-fluoro-5-sulfamoyl-benzoic acid (IV) is precipitated according to common procedures; the obtained precipitate is then collected and extensively washed with water.

The use of dichloromethane as extraction solvent gives the following advantages:

there is no need of filtration in order to isolate the product 4-chloro-2-fluoro-5-chlorosulfonyl-benzoic acid;

the acidity of the organic layer is easily eliminated by washing twice with water.

Step C:

finally, in step (C) of the process according to the present invention, already known in the state of the art, a mixture of (IV) and furfurylamine is heated to 95° C., for a period of 2 hrs, at a furfurylamine/(IV) molar ratio ranging from 2 to 6.

Said reaction can be conducted also in suitable organic solvents, such as 2-methoxy-ethanol or dimethylformamide.

Once the reaction has been completed, the mixture is poured in water and acidified to pH 4 with glacial acetic acid. The crystalline product (I) is separated, washed with water and finally recrystallized from ethanol. Furosemide (I) is obtained in high yields (m.p. 206°–208° C.; yield 96%). The following examples are reported by way of indication, not of limitation, of the present invention.

Preparation of 4-chloro-2-fluoro-benzotrichloride (III) (Step A1

EXAMPLE 1

A 2-liter apparatus equipped for photochlorination, provided with bubbler, thermometer, condenser, mercury-vapour lamp (50 Watt) and gas absorption system, was fed with 4-chloro-2-fluoro-toluene (1,44 g; 10.0 mol) and the product was heated to 90° C. under a gentle nitroge stream. Said lamp was lit up and, a few minutes later, gaseous chlorine was bubbled through the solution at a flow rate of 140 g/h. The reaction started soon, while the rise in temperature was properly controlled. The reaction course was followed by GLC, with the following results:

after 6 hrs and 30 min, the presence of a reaction mixture consisting of 50.4% of dichloro derivative and 48.9% of trichloro derivative was observed;

after 11 hrs, the reaction mixture consisted of 0.3% of dichloro derivative and 98.9% of trichloro derivative.

Once the reaction had been completed, the solution was cooled under a nitrogen stream to eliminate the gases dissolved therein. A raw product (2,459 g; 9.92 mol) was obtained, in yield of 99.2%.

A fraction of said raw product (1,364 g) was fed to a 2-liter flask properly equipped for distillation under vacuum, at a pressure of 5 mmHg. The product was distilled at a top temperature of 170° C. and at a flask temperature of 116° C. to 120° C. 4-Chloro-2-fluoro-benzotrichloride (1,307 g; 5.27 mol) was thus isolated, with a distillation yield of 95.8% and a total yield of 95.0%. The residue in the distillation flask, weighing 48.6 g, is then discarded.

The obtained product, 4-chloro-2-fluoro-benzotrichloride, having a molecular weight of 247.9, exhibited the following characteristics:

Physical state: liquid

Elemental composition:

|   | Calcd.: | Found: |
|---|---------|--------|
| C | 33.91%; | 33.60%; |
| H | 1.22% | 1.23% |
| Cl | 57.20% | 56.90% |
| F | 7.66% | n.d. |

Infrared spectrum: the IR spectrum (KBr pellet) showed the following main absorptions:

| Assignment | Frequency cm$^{-1}$ |
| --- | --- |
| C—H aromatic stretching | 3050 |
| | 3085 |
| | 3110 |
| C=C aromatic stretching | 1570 |
| | 1600 |
| | 1450 |
| | 1480 |
| C—Cl aromatic stretching | 1080 |
| C—H out-of-plane bending | 840 |
| | 860 |
| C—Cl aliphatic stretching | 760 |

Preparation of 4-chloro-2-fluoro-sulfamoylbenzoic acid (IV) (Step B)

EXAMPLE 2a

A 2-liters reactor of stainless steel provided with stirrer, temperature controller, and equipped for reflux was fed with the following reagents:

| | |
| --- | --- |
| 4-chloro-2-fluoro-benzotrichloride (III) | 282 g (1.14 mol) |
| sulfuric chlorohydrin | 1,008 g (8.65 mol) |
| sulfuric acid (96%) | 92 g |

The mixture was slowly heated to 148°–150° C. and allowed to react for 1 hr and 30 min; after cooling to about 30° C., the solution was dropwise added to a mixture containing:

| | |
| --- | --- |
| water | 1,600 ml |
| ice | 1,600 g | while the inner temperature was maintained under control within 0° C. and 2° C., under vigorous stirring in order to obtain a good crystallization. Once said addition had been completed, the mixture was stirred for 5 hrs and filtered. The filtrate was washed with water until wash water neutrality.

After filtration, the crude product, 4-chloro-2-fluoro-5-chlorosulfonylbenzoic acid, exhibited the following characteristics:

raw formula: $C_7H_3FCl_2SO_4$
Elemental analysis:

| | Calcd.: | Found: |
| --- | --- | --- |
| C | 30.79%; | 31.35%; |
| H | 1.11% | 1.08% |
| S | 11.75% | 11.75% |
| Cl | 25.97% | 25.82% |

The solubility in dichloromethane was roughly 1:5 w/v.

After filtration, the wet 4-chloro-2-fluoro-5-chlorosulfonyl-benzoic acid was added in portions to 30% NH$_4$OH (1,800 ml) under good stirring, while the mixture temperature was maintained below 10° C. After completing said addition, the solution was stirred for 2 hrs, added with decolorizing carbon (10 g) and the resulting mixture was filtered. The filtered solution was concentrated under vacuum below 10° C. The obtained solution was slowly acidified with H$_2$SO$_4$ 30% to pH 2.0 and cooled to 0° C. under stirring. A complete product precipitation was obtained. The precipitate was filtered and washed with cold water until complete elimination of sulfates in wash water.

A white to slightly yellow product (IV) was isolated, with a purity of 94–97% as determined by HPLC (yield=65%).

EXAMPLE 2b

A 2-liters reactor of stainless steel provided with stirrer, temperature controller, and equipped for reflux was fed with the following reagents:

| | |
| --- | --- |
| sulfuric chlorohydrin | 1,008 g (8.65 mol) |
| sulfuric acid (96%) | 92 g |

The mixture was heated to 130°–140° C. and then slowly fed in the time of about 2 hrs with:

| | |
| --- | --- |
| 4-chloro-2-fluoro-benzotrichloride (III) | 282 g (1.14 mol) | taking care to entrap the gaseous HCl thus formed. Once the above addition had been completed, the mixture was maintained for further 60 minutes at a temperature of 148°–150° C. (reflux); after cooling to room temperature, the mixture was dropwise added to a mixture of water and ice (3,200 g), while the inner temperature was maintained below 10° C., under vigorous stirring in order to obtain a good crystallization.

After filtration, the wet product was dissolved in dichloromethane (1,600 ml) e the thus obtained solution was washed with cold water. The organic phase was slowly added to 30% NH$_4$OH (1,800 ml), maintaining the mixture temperature in the range of 2°–6° C.

After completing said addition, the solution was stirred for 2 hrs and the aqueous alkaline phase was separated and worked up as decsribed in Example 2a.

A white to slightly yellow product (IV) was isolated, with a purity of 94–97% as determined by HPLC (yield=75%).

Preparation of Furosemide (I) (Step C)

EXAMPLE 3

A reactor of stainless steel provided with stirrer, temperature controller and equipped for reflux was fed with the following reagents:

| | |
| --- | --- |
| 4-chloro-2-fluoro-5-sulfamoyl-benzoic acid (IV) | 50.7 g (0.20 mol) |
| furfurylamine (freshly distilled) | 97.01 g (1.0 mol) |

The mixture was heated to 95° C., under stirring, for a period of 2 hrs, then allowed to cool and poured in 1 liter of water; the obtained mixture was then acidified to pH 4.0 with glacial acetic acid.

The crystallized product was separated, washed with water and recrystallized from EtOH, thus obtaining 63.0 g of furosemide (I) (0.19 mol; yield=94%) showing the following characteristics:

Purity: >99.2%

Elemental composition: found results are in agreement with calculated values.

Physical state: white to slightly yellow, odorless, almost tasteless crystalline powder.

Melting point: 206°–208° C.

Infrared spectrum: the IR spectrum (KBr pellet) showed the following main absorptions:

| Frequency cm$^{-1}$ | Type of vibration | Assignment |
| --- | --- | --- |
| 3350–3400 | NH | C—NH |
| 1671 | C=O | COOH group |
| 1596 | NH | NH$_2$ group |
| 1322 | —S=O | SO$_2$ group |
| 582 | Cl | C—Cl |

We claim:

1. A process for the preparation of furosemide comprising the following steps:

A) 4-chloro-2-fluoro-toluene (II) is photochlorinated to give 4-chloro-2-fluoro-benzotrichloride (III);

B) 4-chloro-2-fluoro-benzotrichloride (III) obtained in step (A) is chlorosulfonylated by treatment with sulfuric chlorohydrin in the presence of sulfuric acid and the resulting product is ammonolyzed by treatment with ammonium hydroxide to give 4-chloro-2-fluoro-5-sulfamoyl-benzoic acid (IV);

C) 4-chloro-2-fluoro-5-sulfamoyl-benzoic acid (IV) obtained in step (B) is condensed with furfurylamine to give furosemide (I).

2. The process according to claim 1, characterized in that, in step (A), the photochlorination is carried out with gaseous chlorine, bubbled at a flow rate of 12 g/h to 16 g/h per mole of (II), at a temperature of 85° C. to 95° C., for a period of 11 to 12 hrs.

3. The process according to claim 1, characterized in that, in step (B), the sulfuric chlorohydrin/4-chloro-2-fluoro-benzotrichloride (III) molar ratio is not lower than 4 and the (III)/sulfuric acid molar ratio ranges from 1.0 to 1.3.

4. The process according to claim 3, characterized in that said sulfuric chlorohydrin/4-chloro-2-fluoro-benzotrichloride (III) molar ratio ranges from 4 to 10.

5. The process according to claim 1, characterized in that, in step (B), the chlorosulfonylation of 4-chloro-2-fluoro-benzotrichloride (III) with sulfuric chlorohydrin is carried out at a temperature of 140° C. to 150° C., for a period of 1 to 3 hrs.

6. The process according to claim 1, characterized in that, in step (B), 4-chloro-2-fluoro-benzotrichloride (III) is added to a mixture of sulfuric chlorohydrin and sulfuric acid preheated at a temperature of 60° to 140° C. and the obtained mixture is then maintained at a temperature of 140° to 150° C., for a period of 1 to 3 hrs.

7. The process according to claim 1, characterized in that, in step (B), the reaction mixture obtained from the chlorosulfonylation of (III) is quenched in water at a temperature of 0° to 2° C. and then maintained at room temperature for a period of 4 to 10 hrs.

8. The process according to claim 7, characterized in that the water mixture obtained by said quenching in water is added with dichloromethane, then the organic phase is separated from the aqueous phase and is treated directly with ammonium hydroxide.

9. The process according to claim 1, characterized in that, in step (B), said treatment with ammonium hydroxide is carried out at an ammonium hydroxide/(III) molar ratio of 13 to 25, at a temperature of 0° to 10° C., for a period of 1–5 to 2 hrs.

10. 4-Chloro-2-fluoro-benzotrichloride of formula (III):

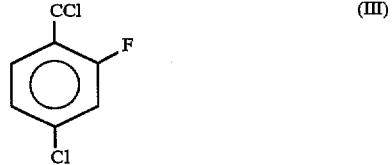

* * * * *